United States Patent
Boppart et al.

(10) Patent No.: US 9,506,858 B2
(45) Date of Patent: Nov. 29, 2016

(54) OPTICAL PARAMETRIC AMPLIFICATION OF WEAK SIGNALS FOR IMAGING BIOLOGICAL TISSUE

(71) Applicant: The Board of Trustees of the University of Illinois, Urbana, IL (US)

(72) Inventors: Stephen A. Boppart, Champaign, IL (US); Youbo Zhao, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 325 days.

(21) Appl. No.: 14/157,840

(22) Filed: Jan. 17, 2014

(65) Prior Publication Data

US 2014/0333925 A1 Nov. 13, 2014

Related U.S. Application Data

(60) Provisional application No. 61/821,642, filed on May 9, 2013.

(51) Int. Cl.
| | |
|---|---|
| *G01J 3/44* | (2006.01) |
| *G01N 21/47* | (2006.01) |
| *G01N 21/64* | (2006.01) |
| *G01N 21/65* | (2006.01) |

(Continued)

(52) U.S. Cl.
CPC ......... *G01N 21/47* (2013.01); *G01N 21/6486* (2013.01); *G01N 21/65* (2013.01); *G02F 1/39* (2013.01); *G02F 1/3534* (2013.01); *G02F 2001/3528* (2013.01); *G02F 2001/392* (2013.01)

(58) Field of Classification Search
CPC .. G01N 21/47; G01N 21/6486; G01N 21/65; G02F 1/39; G02F 1/3534

USPC .......................................................... 356/301
See application file for complete search history.

(56) References Cited

U.S. PATENT DOCUMENTS

| | | | | |
|---|---|---|---|---|
| 5,365,069 A | * | 11/1994 | Eisen | G01T 1/1648 250/363.04 |
| 5,822,061 A | * | 10/1998 | Delhaye | G01J 3/42 356/301 |
| 6,320,886 B1 | * | 11/2001 | Dawber | G01N 21/4795 359/330 |

(Continued)

OTHER PUBLICATIONS

Vaughan et al. ("Optical-parametric-amplification imaging of complex objects", Optics Express, vol. 19 (9), 2011, pp. 8920-8929).*

(Continued)

*Primary Examiner* — Kara E. Geisel
*Assistant Examiner* — Hina F Ayub
(74) *Attorney, Agent, or Firm* — Sunstein Kann Murphy & Timbers LLP (57) ABSTRACT

Methods and apparatus for obtaining an image of light scattering biological tissue. A series of pulses of substantially monochromatic light of a first wavelength is generated and split into two parts, of which one part illuminates a scattering biological tissue at an intensity too low to damage the tissue, while a second part is upconverted to generate a pump beam. Sample light from the biological tissue, which may be scattered (or transmitted) light, or fluorescence, or Raman scattering, etc., is collected and directed from the scattering biological tissue, along with the pump beam, into a non-linear optical element, in a single pass or multiple passes. Parametrically amplified sample light emerging from the non-linear optical element is detected and analyzed or displayed.

20 Claims, 6 Drawing Sheets

(51) Int. Cl.
*G02F 1/39* (2006.01)
*G02F 1/35* (2006.01)

(56) References Cited

U.S. PATENT DOCUMENTS

| | | | | |
|---|---|---|---|---|
| 2001/0017727 | A1* | 8/2001 | Sucha | G01N 21/4795 359/326 |
| 2001/0046244 | A1* | 11/2001 | Klimov | B82Y 20/00 372/50.22 |
| 2002/0176472 | A1* | 11/2002 | Arbore | G02F 1/39 372/72 |
| 2003/0160955 | A1* | 8/2003 | Xie | G01J 3/44 356/301 |
| 2005/0090750 | A1* | 4/2005 | Ediger | A61B 5/0059 600/476 |
| 2005/0105084 | A1* | 5/2005 | Wang | G01J 3/02 356/301 |
| 2005/0238070 | A1* | 10/2005 | Imeshev | G02F 1/3558 372/21 |
| 2006/0192969 | A1* | 8/2006 | Marks | G01J 3/4412 356/451 |
| 2010/0020318 | A1* | 1/2010 | Lee | G01J 3/02 356/301 |
| 2010/0079753 | A1* | 4/2010 | Hehlen | G01J 3/02 356/301 |
| 2010/0321767 | A1* | 12/2010 | Borguet | G02F 1/3544 359/330 |
| 2013/0211391 | A1* | 8/2013 | Benyakar | A61B 18/20 606/10 |
| 2013/0279528 | A1* | 10/2013 | Miesak | H01S 3/10007 372/18 |
| 2013/0279529 | A1* | 10/2013 | Miesak | H01S 3/10 372/25 |
| 2014/0219300 | A1* | 8/2014 | Schimidt | G02F 1/39 372/25 |
| 2015/0036210 | A1* | 2/2015 | Asobe | G02F 1/39 359/341.3 |

OTHER PUBLICATIONS

T.H. Jeys ("Multipass optical parametric amplifier", Optics Letters, vol. 21 (16) 1996, pp. 1229-1231).*
Baumgartner et al., "Optical Parametric Amplification," *IEEE J. Quantum Elect.*, vol. QE-15, No. 6, pp. 432-444 (Jun. 1979).
Cerullo et al., "Ultrafast optical parametric amplifiers," *Rev. Sci. Instrum.*, vol. 74, No. 1, pp. 1-18 (Jan. 2003).
Han et al., "Ultrasensitive femtosecond time-resolved fluorescence spectroscopy for relaxation processes by using parametric amplification," *J. Opt. Soc. Am. B*, vol. 24, No. 7, pp. 1633-1638 (Jul. 2007).
Levenson et al., "Reduction of quantum noise in optical parametric amplification," *J. Opt. Soc. Am. B*, vol. 10, No. 11, pp. 2233-2238 (Nov. 1993).
Zhang et al., "Measurement of the intensity and phase of attojoule femtosecond light pulses using Optical-Parametric-Amplification Cross-Correlation Frequency-Resolved Optical Gating," *Opt. Express*, vol. 11, No. 6, pp. 601-609 (Mar. 2003).

* cited by examiner

OPTICAL PARAMETRIC AMPLIFICATION OF WEAK SIGNALS FOR IMAGING BIOLOGICAL TISSUE

The present application claims priority of U.S. Provisional Patent Application Ser. No. 61/821,642, filed May 9, 2013, and incorporated herein by reference.

This invention was made with government support under Grants CBET 1033906, awarded by the National Science Foundation. The Government has certain rights in the invention.

TECHNICAL FIELD

The present invention relates to apparatus and methods for imaging on the basis of amplifying light derived from a scattering biological sample.

BACKGROUND ART

Imaging of biological tissue, as opposed to analysis of solutions or matrices of various sorts, imposes particular difficulties, primarily because biological tissue is highly scattering at optical wavelengths. Other challenges arise due to unique length and time scales of interest and vulnerability of the tissue to damage in light fields of excessive intensity.

Thus, light signals arising in scattering biological tissue are not only highly attenuated due to propagation though the tissue of both any probe field and the light signal arising in the medium, but, additionally, those weak light signals are characterized by low spatial and temporal coherence, since mean free paths through the medium are extremely short.

Moreover, low light input is always preferable in biological environments so as to limit any possible damage or interference to the biological environment. Currently, detection of these low level light signals has primarily relied on high-sensitivity photo-detectors, e.g. photo multiplier tubes or avalanche photodiodes. However, the sensitivity of these state-of-the-art detectors is reaching their theoretical limit, and fundamentally new technologies are called for in order to further improve detection efficiency.

Various modalities of optical amplification are known for boosting weak light signals, and these may be taken to include such technologies as heterodyne detection, stimulated emission or stimulated Raman scattering amplification, and optical parametric amplification (OPA). And while OPA has been demonstrated to be advantageous in amplification of ultraweak light, due to amplification ratios as high as $10^8$, broad gain bandwidths of up to hundreds of nanometers, and no threshold requirement for the light to be amplified, there are many challenges that suggest that OPA schemes may not be suitable for amplifying signals used for optical imaging of highly scattering biological tissue. First, the phase-matching criteria of OPA require high degree of coherence of light to be amplified, but light signals generated in scattering biological samples usually have low spatial and temporal coherence. In addition, to achieve the high pump intensity required in OPA, pulsed lasers with high peak power but low repetition rate have typically been used. Unfortunately, such conditions are not suitable for practical imaging of biological samples because the low pulse repetition rate results in a long image formation time. These critical challenges have precluded the application of OPA to optical imaging of scattering biological tissue.

SUMMARY OF EMBODIMENTS OF THE INVENTION

In accordance with embodiments of the invention, apparatuses and methods are provided for obtaining an image of scattering biological tissue. One embodiment of a method in accordance with the invention has steps of:

generating a series of pulses of substantially monochromatic light of a first wavelength;

splitting each of the pulses into a first part and a second part;

converting the first part of each pulse into a white light supercontinuum;

illuminating the scattering biological tissue with the white light supercontinuum;

upconverting the second part of each pulse to a generate a pump beam;

collecting sample light from the biological tissue;

directing both the sample light from the scattering biological tissue and the pump beam onto a non-linear optical element; and detecting parametrically amplified sample light emerging from the non-linear optical element.

In accordance with other embodiments of the invention, there may be further steps of imposing a temporal offset of the pump beam relative to the sample light, or temporally resolving the sample light. The pump beam may be characterized by a wavelength that is a harmonic of the substantially monochromatic light of the first wavelength.

In accordance with further embodiments, sample light coherently scattered from the scattering biological tissue due to illumination by the white light supercontinuum may be selectively amplified, and spatial resolution may be enhanced based on selective amplification of coherently scattered light.

In yet further embodiments, the sample light may be backscattered from the scattering biological tissue, or else may be collected from the scattering biological tissue in a forward direction. The sample light may be Raman scattered, either spontaneous or stimulated, or may be resonantly scattered by the scattering biological tissue. The sample light may be fluorescent emission of the scattering biological tissue.

In alternate embodiments of the invention, directing both the sample light from the biological tissue and the pump beam onto the non-linear optical element may include multipassing both the sample light from the scattering biological tissue and the pump beam through the non-linear optical element. Multiple passes of the sample light and pump beam may be differentially delayed, and may include at least three traversals of the non-linear optical element. Generating the series of pulses may include producing pulses at a rate exceeding 200 kHz. Finally, parametric amplification may be achieved by type-I (ooe) phase matching in the second non-linear element.

In accordance with another aspect of the present invention, an apparatus is provided for obtaining an image of scattering biological tissue. The apparatus has a source of pulses of substantially monochromatic light of a first wavelength and a beamsplitter for splitting each of the pulses into a first part and a second part. The apparatus also has a spectral spreader for converting the first part of each pulse into a white light supercontinuum, focusing optics for illuminating the scattering biological tissue with the white light supercontinuum, a first nonlinear optical element for upconverting the second part of each pulse to generate a pump beam, and collection optics for collecting sample light emergent in a backwards direction from the biological tissue. The apparatus has a second non-linear optical element for receiving the sample light and the pump beam and parametrically amplifying the sample light, a detector for receiving parametrically amplified sample light and generating a detector signal, and a processor for generating an image of the scattering biological tissue on the basis of the detector signal.

In other embodiments of the invention, the source of pulses may be a laser, and, more particularly, either a femtosecond laser or a picosecond laser. At least one of the first nonlinear optical element and the second nonlinear optical element may be beta barium borate, and the spectral spreader may be a sapphire plate, although other modalities may be used within the scope of the invention.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

Definitions

The term "scattering medium," as used herein and in any appended claim, shall mean a medium in which an incident electromagnetic wave, of a wavelength range pertinent to the context under discussion, shall be characterized by a mean free path to scatter that is substantially shorter than the dimension of the medium in the propagation direction of the incident electromagnetic wave.

The term "scattering biological tissue," as used herein and in any appended claim, shall mean an organized ensemble of interconnected cells of an organism that has the optical properties associated with a scattering medium, as defined above.

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereon. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

The terms "object," "sample," and "specimen" shall refer, interchangeably, to a tangible, non-transitory physical object capable of being rendered as an image.

When used to modify terms such as "beam," "pulse," etc., the terms "sample" and "signal" are used herein interchangeably.

The term "substantially monochromatic" as applied to a source of irradiation shall refer to a source for which $\Delta k/k_0$ is less than 10%, with $k_0$ denoting the central wavenumber of the spectrum illuminating the sample, while $\Delta k$ denotes the range of illuminating wavenumbers. Insofar as certain pulses falling within the scope of the present invention may be so short in duration that their bandwidth is transform-limited, then the criterion of monochromaticity shall refer to a virtual temporal extension of the pulse such that its bandwidth is no longer governed by pulse duration.

The term "white light supercontinuum" shall refer to a spectrum of light generated through a nonlinear process where the spectrum is characterized by excursions from flatness of the spectral power density no greater than 20 dB over a significant fraction of an octave.

A "harmonic" of a frequency characterizing a light beam shall refer to a whole multiple of that frequency, or, colloquially, a "harmonic" may refer to a beam that bears the stated frequency relationship to another beam.

"Parametrically amplified light" shall mean light amplified through a nonlinear optical process in which the coupling between three waves at frequencies $\omega_p$, $\omega_s$ and $\omega_i$ is governed by a non-zero second-order susceptibility tensor element $\chi_{ijk}^{(2)}(\omega_p, \omega_s, \omega_i)$, and where an intense pump wave at $\omega_p$ generates signal and idler waves at $\omega_s$ and $\omega_i$ respectively.

As used herein and in any appended claims, the term "Raman scattering" encompasses both stimulated and spontaneous processes.

The term "fluorescence," shall be used herein without limitation to encompass any process of emission of one or more photons by a medium from a quantum energetic state (typically real, but including also virtual states) that has been excited by one or more photons of incident radiation. Thus, resonant-enhanced scattering, whether single- or multiple-photon, and whether spontaneous or stimulated, is considered to be subsumed within the term "fluorescence," as that term is used herein.

The term "picosecond laser," as used herein, refers to a laser emitting pulses of duration (full-width-half-maximum, FWHM) between 0.1 ps and 1 ns.

The term "femtosecond laser," as used herein, refers to a laser emitting pulses of duration (FWHM) between 1 fs and 1 ps.

In accordance with embodiments of the present invention, an optical parametric amplifier (OPA) is used to provide significant signal gain in performing a variety of imaging modalities as applied to scattering media, and, in a particularly pertinent (albeit not exclusive) example, to biological tissue. The principles of an OPA, based on a second order optical nonlinear process, are well-known and need not be rehearsed here at any length. The reader is referred, for example, to Levenson et al., *Reduction of Quantum Noise in Optical parametric Amplification*, J. Opt. Soc. Am. B, vol. 10, pp. 2233-38 (1993), which is incorporated herein by reference. Suffice it to say that under the phase-matching condition, a pump photon at optical frequency $\omega_p$ is divided into two daughter photons, called the signal (at $\omega_s$) and idler (at $\omega_i$) by convention, with the sum of their energies $\hbar(\omega_s+\omega_i)$ equal to that of the pump. Incident photons at $\omega_s$ that are coherent with the OPA signal are amplified with coherence properties preserved, accompanied by the generation of an idler beam.

An embodiment of an OPA setup 200, for practice of certain embodiments of the present invention, is now described with reference to FIG. 2. A source 201 emits a beam 203 which is substantially monochromatic in the sense defined above, which is to say that any substantial spectral breadth is due only to the transform-limited spectral breadth of short pulses. Source 201 is typically a laser, and, in a preferred embodiment of the invention, source 201 is a Ti:sapphire regenerative amplifier system, such as model RegA 9000 available from Coherent Inc. of Santa Clara, Calif. Source 201 emits short pulses, on the order of 100 femtoseconds in duration, at 800 nm, with a repetition rate of at least 250 kHz, and pulse energy of about 4 µA although it is to be understood that the pulse duration, repetition rate and energy per pulse, as well as the wavelength of the emitted beam 203 are provided by way of example only, and without limitation. In particular, femtosecond lasers and picosecond lasers are preferred for the embodiments described herein.

Beam 203 is split by beam splitter 205 into a first beam 207 and a second beam 209, where first beam 207 is typically weaker than second beam 209, such as ⅓ of the energy per pulse of the second beam. First beam 207 is focused by focusing optics 211 into a nonlinear element 213, such as sapphire plate, in order to generate a white light supercontinuum 215, then band-pass filtered by bandpass filter BPF. Nonlinear element 213 may also be referred to herein as a "spectral spreader." It is to be understood that, within the scope of the present invention, other modalities, such as photonic crystal fibers, may also be used as a spectral spreader to generate supercontinuum 215. The spectral bandpass of bandpass filter BPF may be 620±30 nm, for example. A resulting illuminating beam 217 is incident, in imaging system 210, on sample 220 via objective 221, which may have a numerical aperture of 0.5, for example. One or more neutral density filters (not shown) may be used to control the incident power of beam 217 onto sample 220.

Meanwhile, second beam 209, having a typical energy of about 3 µJ per pulse, is focused by optic 232 into a non-linear crystal 234, typically a 1-mm thick type I beta barium borate (BBO), to create a frequency-doubled pump beam 236 used as the OPA pump. The optical parametric amplifier is designated generally by numeral 230. Signal beam 227, collimated by returning through objective 221, is combined collinearly with pump beam 236 via dichroic mirror 238 and both beams are mixed together in a second nonlinear element 240, again, typically, 1-mm thick type I beta barium borate (BBO) crystal, to generate the optical parametric process. Parametric amplification is achieved by type-I (ooe) phase matching in the second non-linear element 240. Delay line 242 provides for controlling a relative delay between the sample beam 227 and the pump beam 236.

Signal and pump pulses are separated by dichroic beamsplitter 244 and reinjected into non-linear crystal 240 subject to separately controllable delays provided by respective delay lines 246 and 248. It is to be understood that, within the scope of the present invention, signal beam 227 and pump beam 236 may pass through non-linear crystal 240 once, twice (as shown) or any number of multiple times, for subsequent rounds of optical parametric amplification.

Amplified signal 250, which may be filtered to remove the pump, is then detected by detector 252, generating a detector signal 254 for processing by processor 225, which may include a computer. In certain embodiments of the invention, amplified signal 250 may be coupled into a single-mode or multimode fiber and analyzed spectrometrically, as by a fiber-based spectrometer. Alternatively, for imaging acquisition, the fiber carrying amplified signal 250 may be coupled to a photomultiplier tube (PMT), serving as detector 252. Detector signal 254 may be processed in standard or nonstandard ways, such as by synchronous detection with a lock-in amplifier, etc., all within the scope of the present invention. Standard signal processing techniques include digitization with a data acquisition card (DAQ) and scanning of sample 220, or scanning of light beam 217 under processor control by means of three-axis stage 223. Processor 225 provides for processing of derived images for storage, analysis, and/or display.

Point Scanning

Due to the dispersion property of nonlinear crystal 240, the phase-matching condition for optical parametric amplification can only be met within a small acceptance angle. In wide-field optical imaging schemes, this leads to a finite bandwidth of spatial frequencies that are amplified, thus limiting the achievable spatial resolution (typically on the order of tens of microns, rendering it unsuitable for applications in microscopy). In accordance with embodiments of the present invention, high repetition rates are employed, where "high," in this context, refers to repetition rates exceeding 200 kHz. A concomitant of high repetition rates, in the context of currently existing technology, is the output of relatively low-energy pulse energy. As described herein, the use of high repetition rates results in effectively fast point scanning, thereby overcoming previous limitations of OPA imaging in spatial resolution (wide-field mode), and in low imaging speed and/or shot-to-shot fluctuations of signals arising from the use of high energy laser pulses at low repetition rates (≤1 kHz). To obtain high optical gain based on the low energy pulses, the pump beam 236 is focused into the BBO crystal 240 under a relatively tight focusing condition, which is determined by the optimal balance between the pump intensity (requiring short focal length and tight focusing) and the acceptance angle requirements of the crystal for phase matching (constraining the angle of the focused beam).

Additionally, a double-pass amplification scheme is preferably employed to enhance the signal gain, as described above. Other novel aspects of the various embodiments of the present invention, such as time gating and nonlinear confocal gating, both of which offer important advantages for imaging highly scattering biological sample, are described below.

Improved Signal Detection Sensitivity

Figure 3:
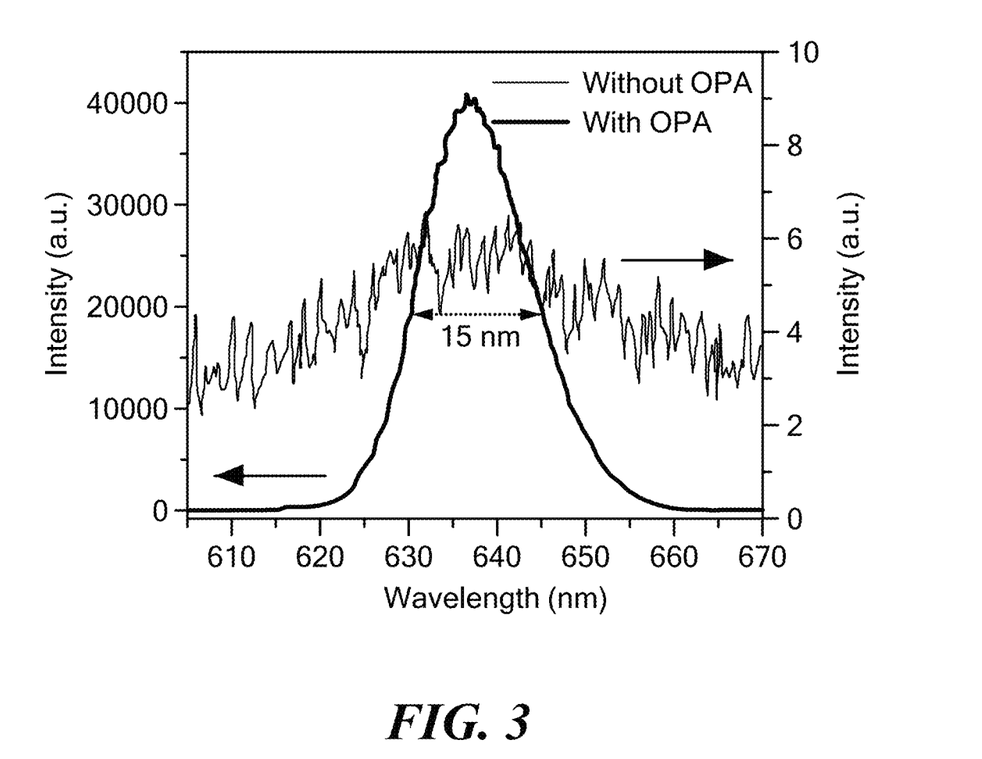
FIG. 3 shows spectra of unamplified and amplified backscattered light from the surface of a scattering medium, in accordance with the present invention, with corresponding scales (in arbitrary units) provided on the right and the left vertical axes, respectively.
Figure 4A:
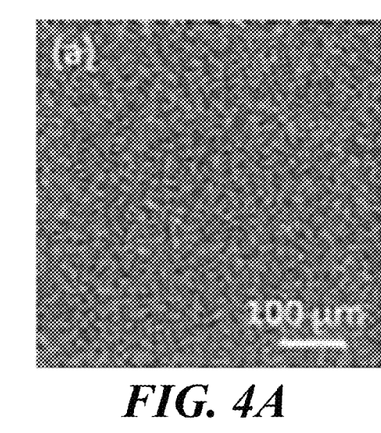
FIGS. 4A-4C show images of onion skin under respective conditions of no amplification, OPA amplification, and no amplification but with a 400-fold increase in light power incident upon the sample.
Figure 4B:
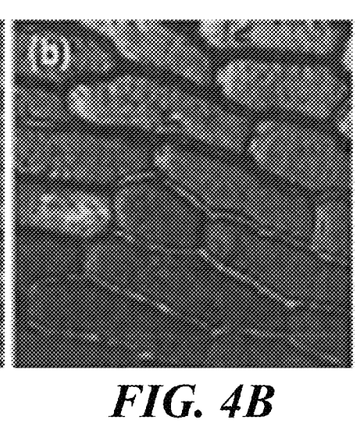
Figure 4C:
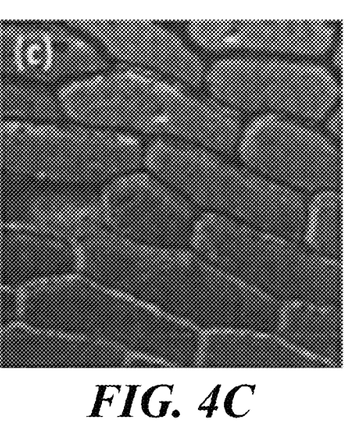

Referring now to FIG. 3, the signal gain provided by the OPA was measured by placing a silver mirror at the focus of an objective of numerical aperture (NA) 0.25. Signal amplification of ~7000×(38 dB) was observed at the peak wavelength of 637 nm, which is widely tunable (from ~500 nm to ~700 nm) by changing the angle of the BBO crystal and the delay between the pump and signal beams. The bandwidth of ~15 nm is determined by the bandwidth of the pump and phase matching within the crystal, and a much broader gain bandwidth is achievable using non-collinear OPAs, which is also within the scope of the present invention For imaging, this OPA gain significantly improves the SNR and thus the image quality, as shown by the comparison of the onion skin images obtained with and without the OPA, as shown in FIGS. 4A-4C. A clear image (FIG. 4B is recovered by the OPA imaging out of the noisy, featureless background (FIG. 4A). FIG. 4C shows an image without amplification but with 400 times higher input light illumination than that employed in deriving FIG. 4A. The significant improvement in the sensitivity of the detection system is because the OPA amplifies the desired signals with negligible excess noise, raising them well above the noise floor, and compensating for poor quantum efficiency of the detector and the signal loss in the light collection apparatus, including the objective, fiber coupling, and other optics. This high ratio of signal gain and improved sensitivity are critical requirements for the cutting-edge optical imaging technologies including deep tissue, single molecule, Raman scattering, and ultrafast imaging and microscopy, where the ultra-weak signals and low SNR are important limiting factors.

Furthermore, improved sensitivity in accordance with the present invention allows for a lower incident light power to be used, decreasing the potential for photo-damage to the sample. The achievable high gain may advantageously obviate the requirement for ultra-sensitive detectors. Due to the large amount of signal gain demonstrated in FIG. 3, the detection sensitivity of the system is significantly improved, by more than two orders of magnitude, depending on the experimental conditions. This is because the OPA boosts the weak signals to compensate for the low quantum efficiency of the PMT, the noise from the PMT and amplifier, and the loss of signal light in the optical collection apparatus, including the fiber, objective, beam splitter and other optics. In a typical case, for example, the quantum efficiency of the PMT is ~3% (at 637 nm), the light signal collection efficiency is approximately 13% (including the ~35% fiber coupling efficiency, 50% loss by the beam splitter, and 76% transmission of the objective, not including. signal light loss in other optics in the beam path. Accordingly, a sensitivity enhancement of 256-fold is to be expected on the basis of OPA compensation for all these inefficiencies and losses. This estimate does not account for contributions from any electronic noise. It should be noted that, although the quantum efficiency can be significantly improved and thermal noise of the detector can be partially removed by detector supercooling (as applied to intensified or EM (electron multiplying) CCDs (charge coupled devices), the loss of light signal in the optical collection system cannot be compensated by any of these electronics devices.

To estimate extra noise added by the OPA process, the incident power was increased to ~14 µW to raise unamplified signals to a similar level as those amplified by the OPA. By comparing the SNRs of the signals due to OPA amplified signals with low incident power with unamplified signals with increased incident power, an ~20% degradation in SNR can be seen in the OPA amplification. The slight discrepancy from the theoretically predicted 3 dB noise (quantum noise) figure, which is associated with this phase-insensitive amplifier may be due to the fact that the SNR of the unamplified signals is larger than the input SNR (presumed noise-free) used for calculating the theoretical noise figure. Because the same detection system was used for these measurements, and because there was no additional noise introduced by adjusting the incident power, the 20% degradation of SNR actually accounts for the contributions from all types of noise added by the OPA, which include the quantum noise and the amplification noise due to the pump laser fluctuations.

It is known that the quantum noise can be potentially suppressed when the OPA operates in a phase-sensitive mode under the degeneracy condition, as described by Baumgartner et al., *Optical Parametric Amplification, IEEE J. Quantum Elect.*, vol. 15, pp. 432-44 (1979), which is incorporated herein by reference. While not part of a preferred embodiment, phase sensitive OPA is within the scope of the present invention.

With enough signal gain, in principle, the OPA has the potential to reach shot-noise limited sensitivity. The sensitivity of the current OPA enhanced detection system was measured to be around 25 fW ($10^{-15}$ Watt) at an integration time of 0.1 ms. This sensitivity is primarily limited by the laser intensity noise (amplitude fluctuations), especially those associated with the signal beam that arise during the supercontinuum (SC) generation process. In principle, this type of laser noise should be removable based on high-frequency modulation, provided that a high repetition rate (such as a few MHz) laser is used.

Shot-noise originates from the quantum nature of photons or electrons. Due to its discretization, the number of photons (n) present at a given time obeys a Poisson probability distribution, for which the standard deviation is given by $\sigma_n=\sqrt{\bar{n}}$. Hence, the shot-noise associated signal-to-noise ratio (SNR) is given by $SNR=\bar{n}/\sigma_n=\sqrt{\bar{n}}$. and the minimum detectable photon number is $\bar{n}=1$. For an integration time of 0.1 ms and a photon wavelength of 637 nm, this corresponds to an optical power of ~3.1 fW.

Although the shot-noise limit may be exceeded, within the scope of the present invention, using techniques such as quantum state squeezed light, it is worthwhile to note that the shot-noise limit may not be a significant barrier in optical imaging. To obtain sufficient contrast in any image, a certain dynamic range of values is required for each pixel. For example, for an 8-bit image, the value of each pixel must be a number between 0 and 255. On average, at least 128 photons are needed to be collected for each pixel, and in this case the shot-noise-limited SNR is 11.3:1, which is a useful SNR in practical imaging, especially considering that many other types of noise can show more influence in the degradation of the SNR. Any signal below the shot-noise limit not only has poor SNR, but also is not sufficiently strong to generate an image with acceptable contrast or dynamic range. In another words, a signal that is well above the shot-noise limited level is desired in order to obtain an image with meaningful contrast. Therefore, in principle, any detection sensitivity close to this limit will be acceptable for imaging, and the most important limiting factor, in practice, is that either the signal is too weak (less than a few photons) or the interference from classical noise, rather than shot-noise, is substantial.

Confocal Gating

In addition to the weak nature of the signals, another fundamental problem in optical imaging of light-scattering biological specimens is the presence of a multiply-scattered light background. Multiply-scattered light is an additional and predominant source of noise that can overwhelm image-bearing ballistic photons and degrade image resolution. In various contexts unrelated to optical amplification, technologies, such as time gating, confocal (spatial) gating, and coherence gating have been employed to filter out the ballistic photons from those that have been multiply-scattered.

In accordance with preferred embodiments of the present invention, the OPA design addresses discrimination against multiply-scattered photons by using gating functions which take advantage of the coherent and nonlinear nature of the optical parametric process. As a result, a nonlinear optical gate is affiliated with the OPA methods in accordance with embodiments of the invention that not only perform the basic functions associated with these gating technologies, but also break the tradeoff between the noise-removal (gating efficiency) and signal-strength, which otherwise imposes the fundamental limit associated with any linear gating technologies.

The OPA gate includes a nonlinear confocal gate and a narrow time gate. The strong confocal gate is generated due to the nonlinear dependence of the amplified signal on the pump and signal intensity, which confines the interaction volume of the OPA in the crystal to the focal region, and thus forms a virtual pinhole. The time gate is determined by the pulse width of the 100 fs pump pulses which has depth-resolved imaging analogous to optical coherence tomography (OCT).

A confocal gate is generated from the nonlinear relationship between the amplified signal and the intensities of the input signal and the pump pulses, which is given by $$I_s = \tfrac{1}{4} I_{s0} \exp(2L\gamma\sqrt{I_p}), \qquad \text{(Eq. 1)}$$

where $\gamma$ is a crystal related constant for fixed frequencies of pump and signal, $I_{s0}$, is the intensity of the input signal, $I_p$ is the intensity of the pump, and L is the phase-matching length. In the low-gain regime (less than 2 for single pass), the exponential relationship may be approximated as a linear function. The foregoing equation may then be simplified as $I_s \sim I_{s0}\sqrt{I_p}$. Under the experimental conditions described above, however, the single-path gain is in the approximate range of 71-84 (5000-7000 for double pass), and the relationship is approximated by $I_s \sim I_{s0} I_p^{4.3}$. These high-order nonlinear relationships confine the OPA process within the focal region, thereby forming a virtual pinhole.

The formation of a virtual pinhole, while shown here for the first time in the case of an optical amplification process, is similar in principle to other known non-linear optical imaging methods. The full-width-at-half-maximum (FWHM) of the intensity point-spread-functions (PSFs), i.e., the diameter of the virtual pinhole in the OPA, are reduced by a factor of $1/\sqrt{1.5}$ and $1/\sqrt{5.3}$ in the low and high gain regimes (described herein by way of example only), respectively, if it is assumed that both the pump and signal beams have a Gaussian shaped focus with the same beam waist.

The nonlinear confocal gating described above offers optical sectioning capability, removal of multiply-scattered background light, and enhancement of lateral resolution, which account for the improved qualities of the OPA images in FIG. 4B 3 compared to the corresponding confocal images. More importantly, due to the exponential relationship between the amplified signal and the intensities of the signal and pump beams (Eq. 1), the higher the pump intensity, the higher order the relationship, and thus the smaller the virtual pinhole and the stronger the amplified signal, because of the higher gain supported by a stronger pump. For a simple illustration, assume that the amplification happens in a thin slab of medium in the plane perpendicular to the propagation direction of the laser beams (z direction) and the beam profiles of both the pump and input signal are Gaussian shaped in the x-y plane (the slab). For simplicity, assume that both the pump and signal have the same waist, which is calculated to be 11.6 µm, and the peak intensity is unity. Based on these assumptions, the diameters of the virtual pinhole can be calculated to be 9.5 µm in the low (less than 2) gain regime, and 5.0 µm for a significantly higher gain, such as 5000-7000 for double-pass. Although this smaller pinhole may not further improve the axial resolution in imaging non-scattering samples, the contributions from the smaller pinhole and the higher gain can be substantial when imaging through scattering media where the multiple-scattering background dominates, because it enables a better efficiency in the detection of ballistic photons and a greater rejection of multiply-scattered background light, as shown by the results in FIG. 4B. This effect is also manifested by the improvement of axial resolution offered by the OPA, compared to conventional confocal imaging.

Temporal Gating

Figure 5A:
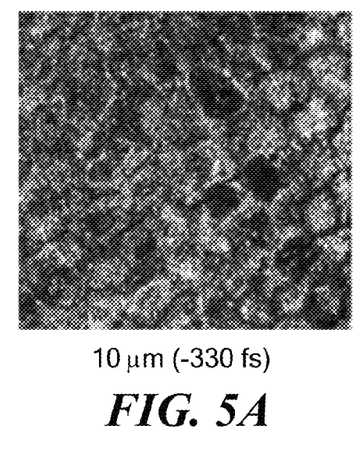
FIGS. 5A-5C show temporal depth gating in en face images of fresh pepper skin with OPA and delays of −330 fs, 0, and 330 fs respectively, between the pump and signal.
Figure 5B:
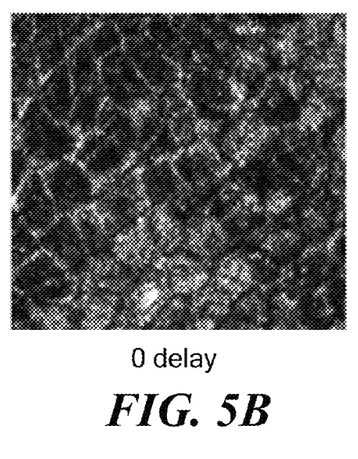
Figure 5C:
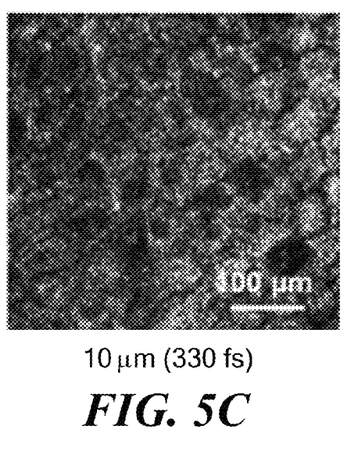

Time gating, in accordance with embodiments of the present invention, is determined by the pulse duration of the pump, which is typically ~100 fs, based on the assumption that the pulses are transform-limited. Temporal gating enables depth-resolved imaging capability and suppression of the multiply-scattered background light. The depth-resolved imaging capability is shown in FIGS. 5A-5C depicting en face images of fresh pepper skin with OPA and delays of −330 fs, 0, and 330 fs respectively, between the pump and signal.

Figure 1A:
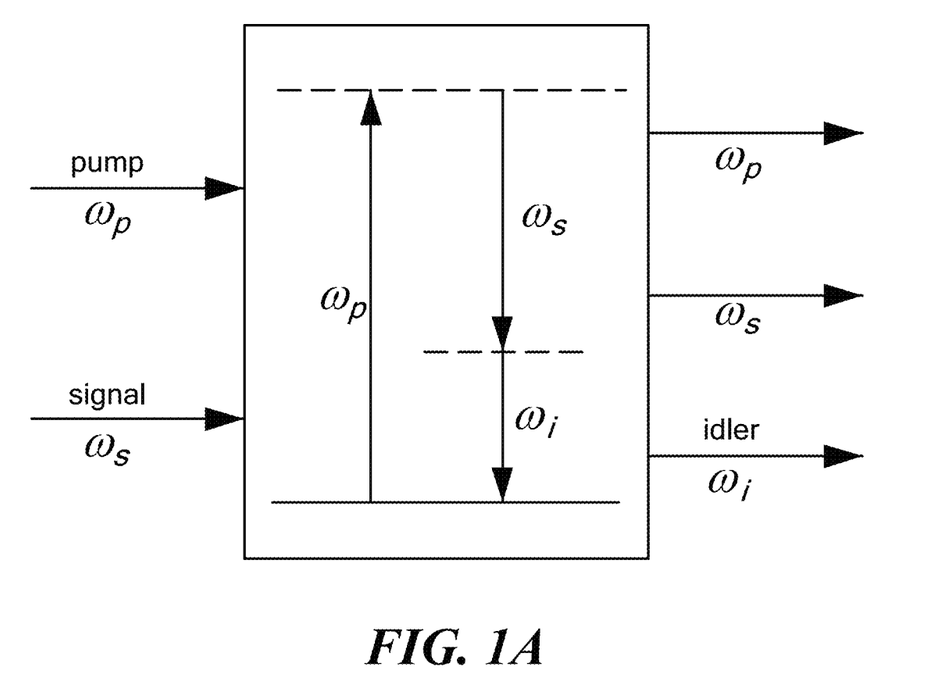
FIG. 1A shows an energy diagram of a non-linear medium in which a parametric amplification process is occurring.
Figure 1B:
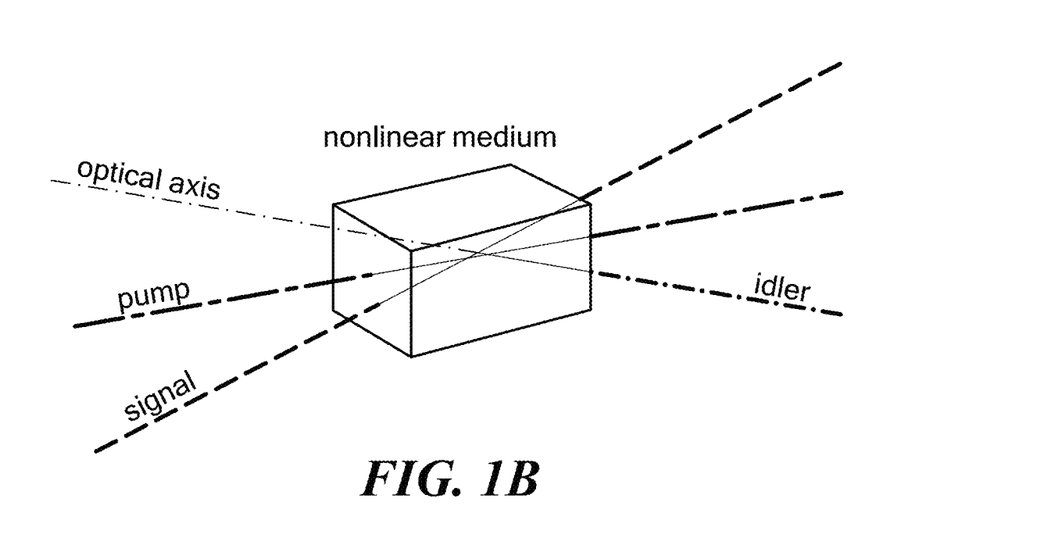
FIG. 1B shows a physical configuration of the waves and the non-linear medium of FIG. 1A.
Figure 2:
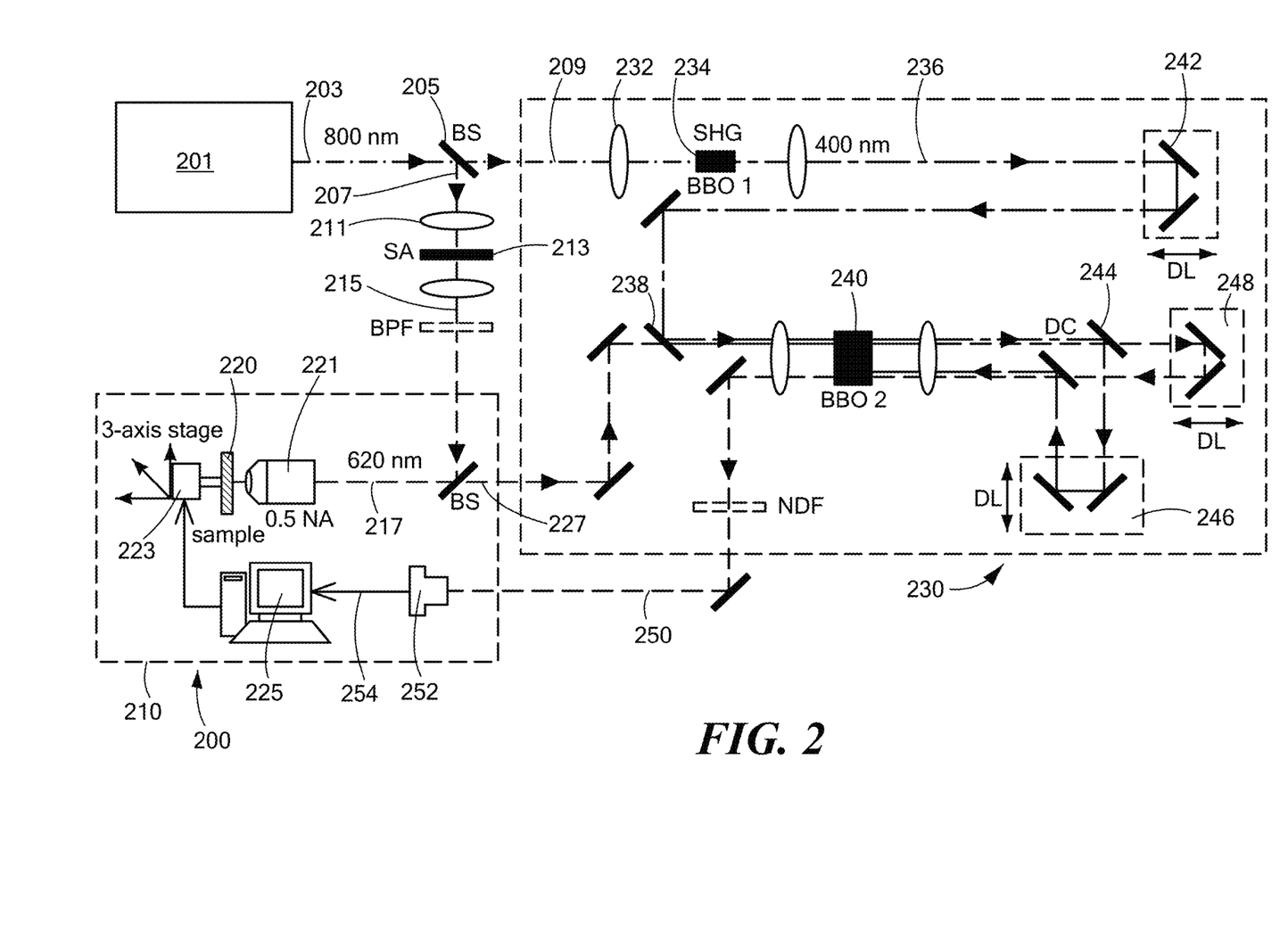
FIG. 2 schematically depicts an optical parametric amplification setup for imaging biological tissue based on backscattering, in accordance with an embodiment of the present invention.
Figure 6:
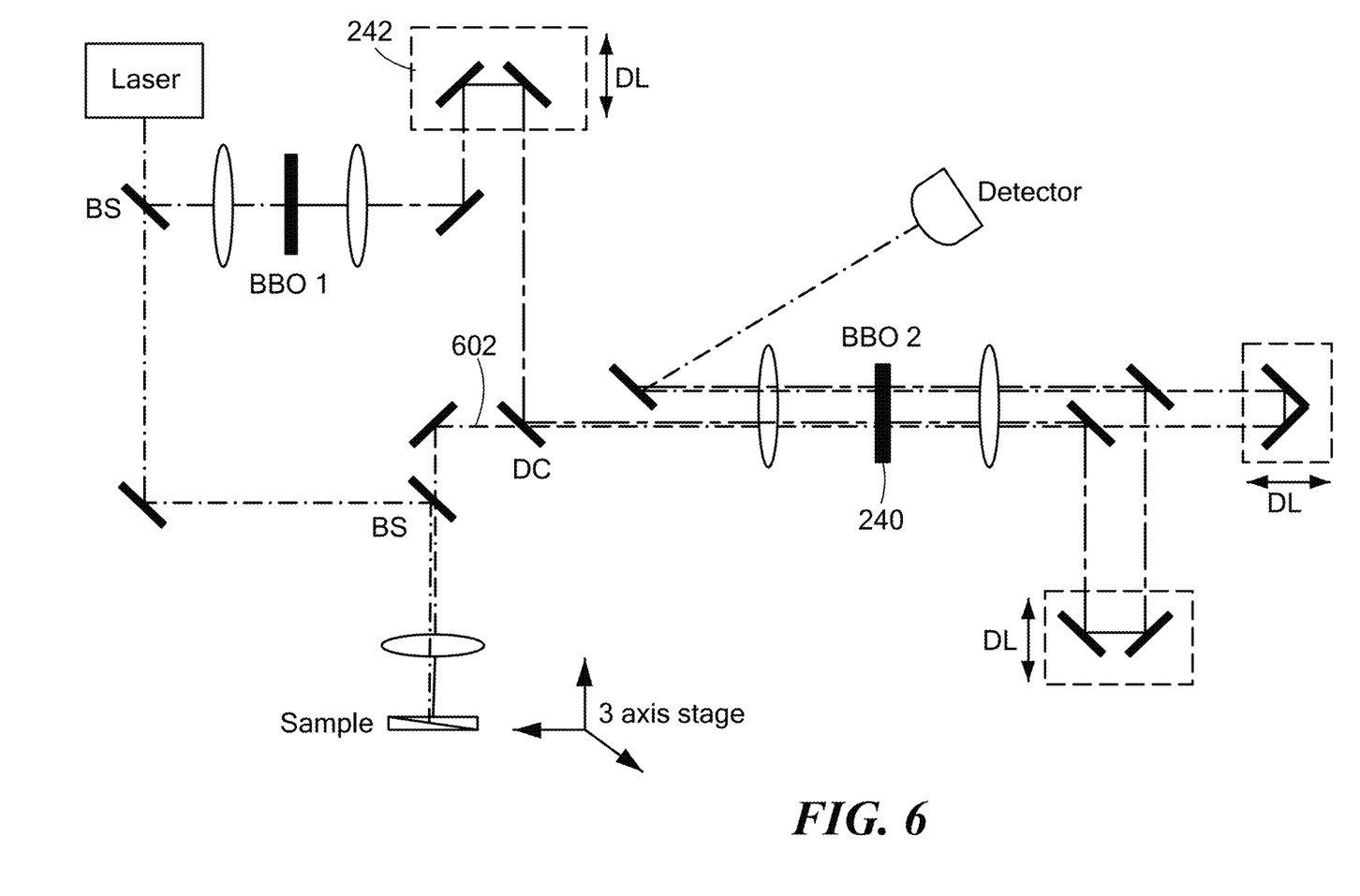
FIG. 6 schematically depicts an optical parametric amplification setup for imaging biological tissue based on two-photon fluorescence, in accordance with an embodiment of the present invention.

The image presented in FIG. 4B was obtained based on the back-scattered light from sample 220 (shown in FIG. 2). It is to be understood that the OPA of fluorescence and Raman scattering signals (whether stimulated or spontaneous) may similarly be used for imaging biological samples, in accordance with other embodiments of the present invention. In the fluorescence OPA embodiments described now with reference to FIG. 6, sapphire plate 213 in the setup shown in FIG. 2 is removed, and beam 203 (typically at 800 nm) is focused onto sample 220 to generate two-photon fluorescence 602 (shown in FIG. 6). The fluorescence signal 602 propagates along the same path as back-scattered light and is amplified by the OPA in nonlinear crystal 240. In fluorescence experiments, not only may high ratio amplification of the fluorescence signal be observed, but, additionally, the lifetime of the fluorescence may be measured by controlling the delay 242 between the pump and the signal, and this femtosecond time resolved fluorescence lifetime information advantageously allows one to observe many new ultrafast dynamics of biological activities at a molecular level.

Figure 7:
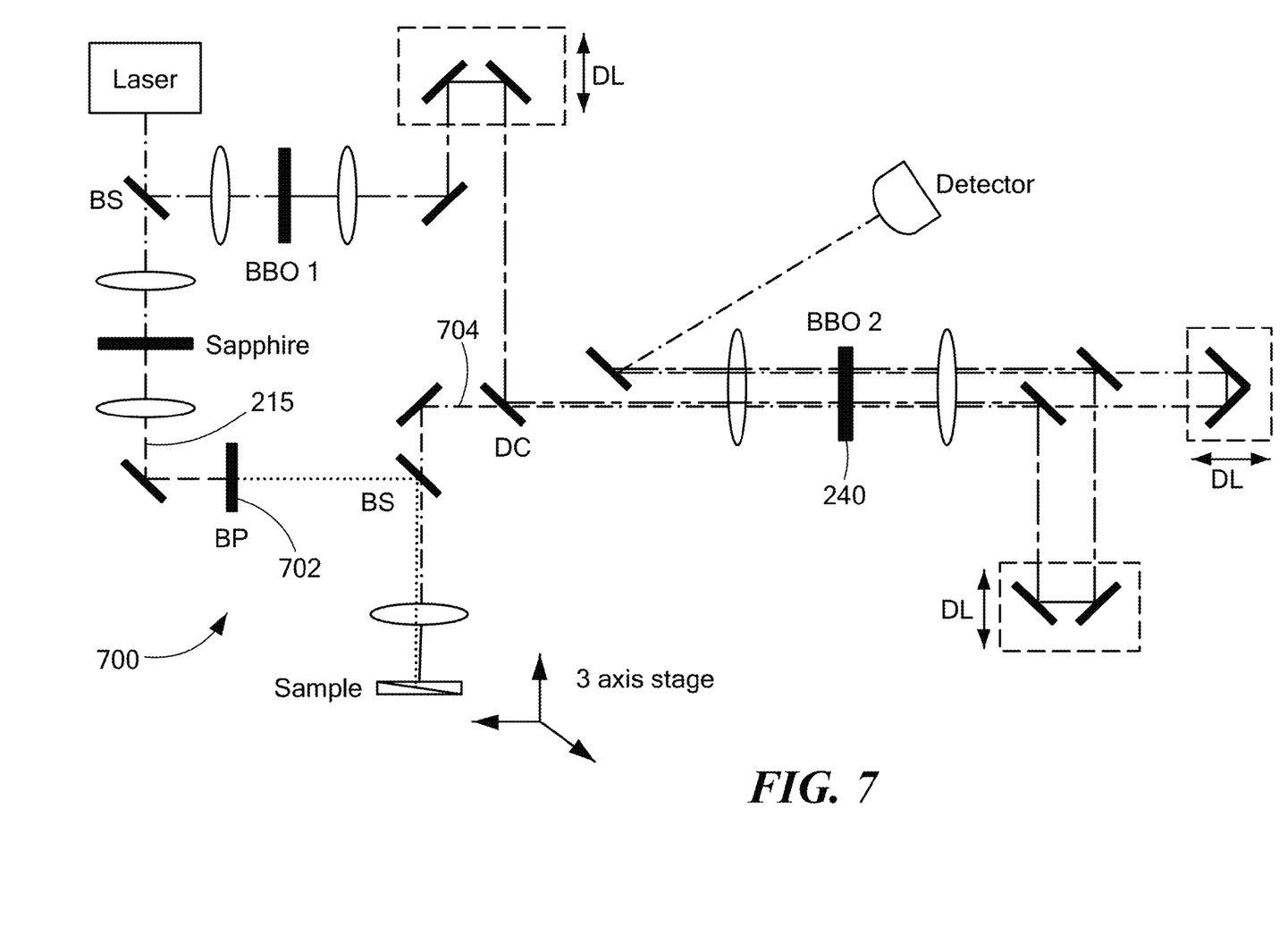
FIG. 7 schematically depicts an optical parametric amplification setup for imaging biological tissue based on Raman scattering, in accordance with an embodiment of the present invention.

Application of OPA to a Raman scattering signal (stimulated or spontaneous), in accordance with further embodiments of the present invention, are more similar to the case of back-scattering imaging than is fluorescence, as shown in in a schematic depictions of a Raman scattering OPA apparatus in FIG. 7. A salient difference between Raman scattering OPA apparatus, designated generally by numeral 700, is that a narrow bandpass filter 702 is placed in the supercontinuum white light beam 215 to select an appropriate wavelength to excite the Raman signal. The Raman scattering signals 704 propagating along the same beam path as the back-scattered light are amplified by OPA for imaging. In this case, the wavelength tunability of the OPA allows larger-width or entire Raman spectra to be obtained, rather than narrow bands in other currently used coherent Raman microscopes, such as coherent anti-Stokes Raman scattering and stimulated Raman scattering microscopy.

In accordance with certain embodiments of the present invention, aspects of the analysis of optical parametric amplification may be implemented as a computer program product for use with a computer system. Such implementations may include a series of computer instructions fixed either on a tangible medium, which is preferably non-transient and substantially immutable, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for obtaining an image of scattering biological tissue, the method comprising:
   a. generating a series of pulses of substantially monochromatic light of a first wavelength;
   b. splitting each of the pulses into a first part and a second part;
   c. converting the first part of each pulse into a white light supercontinuum;
   d. illuminating the scattering biological tissue with the white light supercontinuum;
   e. upconverting the second part of each pulse to a generate a pump beam;
   f. collecting both ballistic and multiply scattered sample light from the biological tissue;
   g. forming a virtual pinhole by directing both the ballistic and multiply scattered sample light from the scattering biological tissue and the pump beam onto a non-linear optical element; and
   h. selectively detecting parametrically amplified ballistic sample light emerging from the non-linear optical element.

2. A method in accordance with claim 1, further comprising imposing a temporal offset of the pump beam relative to the ballistic and multiply scattered sample light.

3. A method in accordance with claim 2, further comprising temporally resolving the ballistic and multiply scattered sample light.

4. A method in accordance with claim 1, wherein the pump beam is characterized by a wavelength that is a harmonic of the substantially monochromatic light of the first wavelength.

5. A method in accordance with claim 1, further comprising enhancing spatial resolution based on selective amplification of coherently scattered light.

6. A method in accordance with claim 1, wherein the ballistic and multiply scattered sample light is backscattered from the scattering biological tissue.

7. A method in accordance with claim 1, wherein the ballistic and multiply scattered sample light is Raman scattered.

8. A method in accordance with claim 7, wherein the ballistic and multiply scattered sample light is spontaneously Raman scattered.

9. A method in accordance with claim 1, wherein the sample light is a fluorescent emission of the scattering biological tissue.

10. A method in accordance with claim 1, wherein directing both the ballistic and multiply scattered sample light from the biological tissue and the pump beam onto the non-linear optical element includes multipassing both the ballistic and multiply scattered sample light from the scattering biological tissue and the pump beam through the non-linear optical element.

11. A method in accordance with claim 10, wherein multiple passes of the ballistic and multiply scattered sample light and pump beam are differentially delayed.

12. A method in accordance with claim 10, wherein multipassing includes at least three traversals of the non-linear optical element.

13. A method in accordance with claim 1, wherein generating a series of pulses includes producing pulses at a rate exceeding 200 kHz.

14. A method in accordance with claim 1, wherein parametric amplification is achieved by type-I (ooe) phase matching in the second non-linear element.

15. An apparatus for obtaining an image of scattering biological tissue, the apparatus comprising:
   a. a source of pulses of substantially monochromatic light of a first wavelength;
   b. a beamsplitter for splitting each of the pulses into a first part and a second part;
   c. a spectral spreader for converting the first part of each pulse into a white light supercontinuum;
   d. focusing optics for illuminating the scattering biological tissue with the white light supercontinuum;
   e. a first non-linear optical element for upconverting the second part of each pulse to generate a pump beam;
   f. collection optics for collecting ballistic and multiply scattered sample light emergent in a backwards direction from the biological tissue; and
   g. a second non-linear optical element, characterized by an aperture-limiting virtual pinhole, for receiving the ballistic and multiply scattered sample light and the pump beam and parametrically amplifying the sample light;
   h. a detector for receiving parametrically amplified sample light and generating a detector signal; and
   i. a processor for generating an image of the scattering biological tissue on the basis of the detector signal.

16. An apparatus in accordance with claim 15, wherein the source of pulses is a laser.

17. An apparatus in accordance with claim 15 wherein the source of pulses is a femtosecond laser.

18. An apparatus in accordance with claim 15 wherein the source of pulses is a picosecond laser.

19. An apparatus in accordance with claim 15, wherein at least one of the first non-linear optical element and the second non-linear optical element is beta barium borate.

20. An apparatus in accordance with claim 15, wherein the spectral spreader is a sapphire plate.

\* \* \* \* \*